United States Patent [19]

Aoki

[11] Patent Number: 5,561,026
[45] Date of Patent: Oct. 1, 1996

[54] PHOTOSENSITIVE MATERIALS COMPRISING FULLERENE

[75] Inventor: Nobuo Aoki, Yokohama, Japan

[73] Assignee: Nippon Oil Co., Ltd., Japan

[21] Appl. No.: 80,410

[22] Filed: Jun. 21, 1993

[30] Foreign Application Priority Data

Jun. 30, 1992 [JP] Japan ................. 4-196572
Nov. 30, 1992 [JP] Japan ................. 4-343296

[51] Int. Cl.⁶ ..................... G03F 7/012; G03F 7/027
[52] U.S. Cl. ............... 430/196; 430/167; 430/197; 430/270.1; 430/280.1; 430/283.1; 430/942; 430/966
[58] Field of Search .................... 430/197, 167, 430/286, 287, 906, 270, 196, 280, 283, 942, 966, 270

[56] References Cited

U.S. PATENT DOCUMENTS 5,178,980  1/1993  Mort et al. .................. 430/71
5,215,841  6/1993  Scharfe et al. ............... 430/58
5,250,378 10/1993  Wang ........................ 430/56

*Primary Examiner*—John S. Y. Chu
*Attorney, Agent, or Firm*—Ostrolenk, Faber, Gerb & Soffen, LLP

[57] ABSTRACT

A photosensitive material comprising a photosensitive-group-containing fullerene such as a photosensitive material which is obtained by adding a photosensitive group to fullerene and/or a photosensitive material which is obtained by combining the fullerene with a photosensitive agent is provided. The photosensitive material according to the present invention has excellent properties as a new resist which is a photosensitive material suitable as a photolithographic resist for the production of semiconductors utilizing such light source as ultraviolet light, deep ultraviolet light, X-ray or electron beam and which meets the requirements for realization of a higher level of resolution and sensitivity.

9 Claims, No Drawings

PHOTOSENSITIVE MATERIALS COMPRISING FULLERENE

BACKGROUND OF THE INVENTION

1. Field of the Invention

The present invention relates to photosensitive materials and more particularly to photosensitive materials suitable for the production of semiconductors such as LSI. Furthermore the present invention relates most particularly to photosensitive materials suitable as photolithographic resists for the production of semiconductors utilizing such light source as ultraviolet light, deep ultraviolet light, X-ray or electron beam, etc.

2. Background Art

Heretofore, the resists for semiconductors, which have been widely used, are positive resists made by combining a novolac-type phenolic resin (hereinafter referred to as novolac resin) with a quinone diazido compound that is a photosensitive component for such light sources as g-ray (436 nm), i-ray (366 nm) and KrF excimer laser (248 nm) as well as positive resists made by combining a novolac resin with a poly-2-methylpentene-1-sulfone as a photosensitive component for X-ray or electron beam.

SUMMARY OF THE INVENTION

Recently, patterns for semiconductor devices such as LSI are becoming smaller and smaller, and the requirements of photolithography are becoming more stringent every year. Presently, the required resists are those which enable such high-resolution pattern formation that has a minimum line width of half micron (0.5 μm) and even quarter micron (0.25 μm). In addition, in order to enhance the productivity still more, resists having a higher level of sensitivity are required. The above-mentioned resists, however, cannot sufficiently meet such requirements. Therefore, in the field of semiconductors, there is a strong demand for the advent of new resists that can meet the requirements for the realization of higher level of resolution and sensitivity.

The present invention is to solve the above-mentioned problems and to provide resists having higher level of resolution and sensitivity. That is, the present invention provides photosensitive materials comprising fullerenes containing photosensitive groups.

DETAILED DESCRIPTION OF THE PREFERRED EMBODIMENTS

In the present invention, fullerene means a carbon allotrope which is also called carbon cluster. The fullerenes hitherto known are those having such molecular formulas as $C_{60}$, $C_{70}$, $C_{76}$, $C_{78}$, $C_{82}$, $C_{84}$, $C_{90}$, $C_{96}$, etc. In the present invention, a mixture can be used which comprises two or more of these fullerenes. Of these, preferred for use in the present invention are $C_{60}$ and $C_{70}$, and particularly preferred is $C_{60}$.

The fullerenes useful in the present invention, i.e., carbon clusters and derivatives thereof, are not limited since any of them can be used. However, raised as preferred fullerenes in addition to the above-mentioned carbon clusters are an alkylamine modified carbon cluster, an alkyl-radical modified carbon cluster and a halogen-element modified carbon cluster. Besides, raised as preferred fullerenes because of excellence in film forming properties are an alkylamine modified carbon cluster and an alkyl-radical modified carbon cluster. The most preferred fullerene for use in the present invention is an alkylamine modified carbon cluster.

As the above-mentioned alkylamines, use can be made of any ordinary alkyl-bearing amines without any special limitation, including primary amines, secondary amines and tertiary amines, with primary amines being particularly preferred because of better addition reactivity thereof to carbon cluster relative to secondary amines or tertiary amines. Preferred alkyl radicals are normally those having 1 to 24 carbon atoms, those having 1 to 12 carbon atoms being particularly preferred.

Preferred alkyl amines include ethylamine, n-propylamine, n-butylamine, t-butylamine, n-hexylamine, 2-ethylhexylamine, n-dodecylamine and aniline. Among these, particularly preferred are n-butylamine, n-hexylamine and 2-ethylhexylamine.

The method of adding alkylamines to carbon cluster is not particularly limited. For example, an alkylamine modified carbon cluster is obtained by first dissolving carbon cluster in an alkylamine and then stirring the mixture for 0.2 to 50 hours.

The amounts of alkylamine to be added can be selected depending on the kinds of the alkyl radicals. Normally the amounts are 5 to 100% by weight, preferably 10 to 60% by weight, more preferably 20 to 40% by weight, based on the weight of carbon cluster. Amounts less than 5% by weight cannot provide sufficient film forming properties, whereas amounts more than 100% by weight cannot lead to sufficient effect of the present invention.

In the present invention, normally one kind of the abovementioned fullerenes is used, but a mixture comprising two or more kinds of fullerenes can be used as necessary.

As for the kinds of photo-activated reaction, generally known are crosslinking type(negative) and disintegrating type(positive), any of which can be used in the present invention, with the crosslinking reaction type being preferred.

In the present invention, the photosensitive materials comprising fullerenes containing photosensitive groups are those obtained by adding photosensitive groups to the fullerene and/or those obtained by combining the fullerene with photosensitive agents.

In the present invention, the photosensitive groups are not particularly limited and all of the functional groups that cause chemical reaction as a result of irradiation with ultraviolet light, deep ultraviolet light, X-ray, electron beam, etc. can be used. Among these, preferred are an acryloyl group, a methacryloyl group, a vinyl group and an epoxy group, with an acryloyl group and a methacryloyl group being particularly preferred. Normally one kind of the photosensitive groups is added, but two or more kinds can also be added as necessary.

The method of adding photosensitive groups to carbon cluster is not particularly limited and an ordinary chemical reaction can be adopted. For example, fullerene in an alkylamine is stirred for several hours at room temperature to produce an alkylamine modified carbon cluster and then the resultant adduct is caused to react with methacrylchloride for several hours, thereby synthesizing a photosensitive material having methyacrylamide group as a photosensitive group.

The amounts of the photosensitive group can be selected depending on the reactivity of the photosensitive group. Normally the practical amounts are 0.1 to 10 moles, preferably 0.3 to 5 moles and most preferably 0.5 to 3 moles, per mole of fullerene. Amounts less than 0.1 mole cannot provide sufficient photosensitivity, whereas amounts more than 10 moles lower the storage stability.

In the present invention, the photosensitive agents to be combined with fullerene are not particularly limited, and all of the photosensitive agents that cause chemical reaction as a result of irradiation with ultraviolet light, deep ultraviolet light, X-ray, electron beam, etc. can be used. Among these, preferred are multi-functional photosensitive agents having two or more photosensitive groups in the molecule thereof. Also, combinations of two or more photosensitive agents can be used as necessary.

Among the photosensitive agents usable in the present invention, preferred are azido compounds.

Illustrative of the azido compounds are 4-azidobenzalacetophenone, 4-azidobenzal-4'-methylacetophenone, 4-azidobenzal-4'-methylacetophenone, 4,4'-diazidobenzalacetophenone, 4-azidobenzophenone, 2,6-di(4'-azidobenzal)cyclohexanone, 2,6-di(4'-azidobenzal)-4-methylcyclohexanone, 2,6-di(4'-azidobenzal)-4-t-amylcyclohexanone, 4,4'-diazidodiphenylsulfone, 4,4'-diazidodiphenylether, 4,4'-diazidophenylsulfide and 4,4'-diazidodiphenylmethane.

Among these, particularly preferred azido compounds are bifunctional ones which are 4,4'-diazidobenzalacetophenone, 4-azidobenzophenone, 2,6-di(4'-azidobenzal)cyclohexanone, 2,6-di(4'-azidobenzal)-4-methylcyclohexanone, 2,6-di(4'-azidobenzal)-4-t-amylcyclohexanone, 4,4'-diazidodiphenylsulfone, 4,4'-diazidodiphenylether, 4,4'-diazidophenylsulfide and 4,4'-diazidodiphenylmethane.

In the photosensitive materials of the present invention, the amounts of photosensitive agent versus fullerene can be selected depending on the photoreactivity of the photosensitive agent and kinds of light sources to be used for the exposure. Normally the amounts are 0.3 to 20% by weight, preferably 1 to 15% by weight based on the weight of fullerene. Amounts less than 0.3% by weight cannot provide sufficient photoreactivity, whereas amounts more than 20% by weight lower storage stability.

If necessary, such resins as polystyrene and phenolic resins can be used in combination with the photosensitive materials of the present invention. However, in order to fully develop the effect of the present invention, it is desirable for the amounts of these resins not to exceed 20% by weight.

One of the features of the photosensitive material of the present invention is the very high resistance to dry etching relative to conventional photosensitive materials. For example, the photosensitive material of the present invention has 30 to 60 times higher resistance to reactive-ion etching by use of $CF_4$ gas than conventional photosensitive materials. Because of this, the film of the photosensitive material of the present invention can be as thin as one-to-tens relative to conventional one. Because of this, the photosensitive material of the present invention exhibits a markedly higher resolution and sensitivity than that of the conventional photosensitive materials.

In the case of the photosensitive material of the present invention, the film thickness of the coating for use is normally 2 to 200 nm, preferably 5 to 100 nm and most preferably 10 to 50 nm. A film thickness less than 2 nm tends to lower the uniformity of the thin film slightly, whereas a film thickness more than 200 nm cannot develop the features of the present invention to the full extent.

As for the method of film formation, spin coating is the most preferred, although many other methods can be employed which include vapor deposition and so on. In the case of the spin coating, a solution of photosensitive material of the present invention is applied. Although all of the solvents which can dissolve the photosensitive materials of the present invention can be used, preferred are aromatic solvents, among which the particularly preferred are toluene, xylene, pseudocumene, etc. The concentration is normally 0.1 to 1% by weight, although the concentration is adjusted in accordance with the film thickness to be formed.

In the present invention, the light sources are not particularly limited because the photosensitive materials of the present invention exhibits high resolution and high sensitivity to a variety of light sources including ultraviolet light, deep ultraviolet light, X-ray and electron beam, etc. X-ray and electron beam have particularly high effect on the photosensitive materials of the present invention.

The conditions for development that comes after exposure can be selected depending on the kinds of photosensitive groups. When the photosensitive material of the present invention is used as a negative one, the preferred developers are aromatic solvents, among which the particularly preferred are toluene and xylene. Although there are no limitations as to the temperatures and periods of time for the development, the normal practice is the immersion for 30 to 200 seconds at temperatures of 20° to 30° C.

The following examples are set forth to illustrate the present invention and are not to be construed as limiting the scope of the invention thereto.

EXAMPLE 1

A 200 ml flask fitted with a stirrer was charged with 0.2 g of high-purity(99.8% purity) C60 and 100 g of n-propylamine. The mixture was stirred at 20° C. for one hour. After the reaction, the excess n-propylamine was distilled off to obtain the reaction product which was proved to be an n-propylamine modified C60 comprising on average 1.2 units of n-propylamine per molecule of C60 as a result of elementary analysis and NMR analysis. The adduct was further reacted with methacrylchloride in toluene to obtain a resist comprising on average 1.2 units represented by the following formula per molecule of C60:

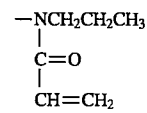

COMPARATIVE EXAMPLE 1

A 300 ml separable flask was charged with 11.4 g of phenol, 26.1 g of m-cresol, 28.5 g of 37% aqueous solution of formaldehyde, 0.61 g of oxalic acid dihydrate, 3.6 g of deionized water and 12.0 g of ethylcellosolve acetate. The mixture was caused to react under stirring at 110° C. for 3 hours. After the aftertreatment, the ethylcellosolve acetate was distilled off to recover the novolac resin which had an average molecular weight of 13,000. A resist was prepared by uniformly blending 90 parts by weight of the novolac resin with 10 parts by weight of poly-2-methylpentene-1-sulfone having an average molecular weight of 82,000.

<Evaluation of the resist performance>

(Resist of Example 1)

A film of photosensitive material, which had been produced in the example of synthesis, having a thickness of 22.0 nm was prepared by spin-coating a 0.5% by weight solution of the resist of the synthesis example in pseudocumene on a silicon wafer and then pre-heating the coating.

The resist was exposed to a predetermined dosage of electron beam, and then subjected to the 1 minute development with toluene to prepare a sensitivity curve. In this manner, the level of sensitivity (a smaller value giving a higher level of sensitivity) and γ value (a larger value giving a higher level of resolution) which was indicative of resolution were obtained.

(Resist of Comparative Example 1)

In a similar way, a film of photosensitive material, which had been produced in the comparative example of synthesis, having a thickness of 1200 nm was prepared by use of ethylcellosolve acetate solution containing 10% by weight of the resist of the comparative example of synthesis. After exposure to electron beam and 1 minute development with an aqueous alkaline solution which followed, sensitivity level and γ value were sought as in the case of example of synthesis.

TABLE 1

Evaluation results of electron beam - resist performance

| | Sensitivity ($\mu C/cm^2$) | γ value |
|---|---|---|
| Resist of Example 1 | 0.024 | 12.1 |
| Resist of Comparative Example 1 | 3.5 | 2.9 |

As is clear from Table 1, the resist of Example 1 has a very high level of sensitivity and resolution.

<$CF_4$ reactive-ion etching test>

The films for testing were prepared as in the case of evaluation of resist performance. The resist of Example 1, which was a negative type, was exposed to the dosage of electron beam corresponding to sensitivity and subjected to development prior to the etching test. The resist of Comparative Example 1, which was a positive type, was subjected to development without exposure prior to the etching test.

The etching test was conducted under the condition of $CF_4$ gas pressure of 0.10 torr. and an output power of 100 W by use of the reactive-ion etching apparatus, RIE-1, manufactured by Samco Company.

TABLE 2

Results of $CF_4$ reactive-ion etching test

| | Initial film thickness (nm) | Etching rate (nm/min) | Length of time in which the film withstands in etching (min) |
|---|---|---|---|
| Resist of Example 1 | 22.0 | 2.1 | 11 |
| Resist of Comparative Example 1 | 1200 | 130 | 10 |

As is clear from Table 2, the resist of Example 1 has an etching resistance which is about 60 times that of the resist of Comparative Example 1. Because of this, despite the far thinner film thickness, in the case of the resist of Example 1, the length of time in which the film withstands etching (before the film thickness is reduced to zero) is equivalent to that of the resist of Comparative Example 1.

EXAMPLE 2

0.5 g of high-purity C60 (99.8% purity, produced by Vacuum Metallurgy Company) and 50 g of n-hexylamine were mixed and the mixture was stirred at room temperature for one hour. Then, methanol was added to the mixture, and the resultant precipitate was recovered by filtration. The precipitate, after being washed with methanol, was vacuum-dried to provide a brown product which was proved to be an n-hexylamine modified C60 comprising 29% by weight n-hexylamine per C60 as a result of elementary analysis and mass spectrometry. 0.3 g of the brown precipitate and 0.03 g of 2,6-di(4'-azidobenzal)- 4-methylcyclohexanone were dissolved in 100 g of toluene to obtain a uniform solution. The solution was spin-coated on a silicon wafer and then pre-heated to form a thin resist film having a thickness of 32.1 nm.

The resist was exposed to a predetermined dosage of electron beam, and then subjected to the 1 minute development with toluene to prepare a sensitivity curve to obtain the level of sensitivity (a smaller value giving a higher level of sensitivity) and γ value (a larger value giving a higher level of resolution). The results are shown in Table 3.

COMPARATIVE EXAMPLE 2

A 300 ml separable flask was charged with 11.4 g of phenol, 26.1 g of m-cresol, 28.5 g of 37% aqueous solution of formaldehyde, 0.61 g of oxalic acid dihydrate, 3.6 g of deionized water and 12.0 g ethylcellosolve acetate. The mixture was caused to react under stirring at 110° C. for 3 hours. After the aftertreatment, the excess ethylcellosolve acetate was distilled off to recover the novolac resin which had an average molecular weight of 13,000. A resist was prepared by uniformly blending 90 parts by weight of the obtained novolac resin with 10 parts by weight of poly-2-methylpentene- 1-sulfone having an average molecular weight of 82,000. A film of photosensitive material having a thickness of 1200 nm was prepared by use of a ethylcellosolve acetate solution containing 10% by weight of the resist obtained in the above. After exposure to electron beam and 1 minute development with an aqueous alkaline solution which followed, sensitivity level and γ value were sought as in the case of example. The results are shown in Table 3.

TABLE 3

Evaluation results of electron beam - resist performance

| | Sensitivity ($\mu C/cm^2$) | γ value |
|---|---|---|
| Resist of Example | 0.023 | 11.2 |
| Resist of Comparative Example | 3.5 | 2.9 |

As is clear from Table 3, the resist of Example 2 has a very high level of sensitivity and resolution.

In the same manner as previously described, $CF_4$ reactive-ion etching test was conducted. The results are shown in Table 4.

TABLE 4

| | Initial film thickness (nm) | Etching rate (nm/min) | Length of time in which the film withstands in etching (min) |
|---|---|---|---|
| Results of CF₄ reactive-ion etching test | | | |
| Resist of Example | 32.1 | 2.9 | 11 |
| Resist of Comparative Example 1 | 1200 | 130 | 10 |

As is clear from Table 4, the resist of Example 2 has an etching resistance which is about 60 times that of the resist of Comparative Example 2. Because of this, despite the far thinner film thickness in the case of the resist of Example 2, the length of time in which the film withstands etching (before the film thickness is reduced to zero) is equivalent to that of the resist of Comparative Example 2.

As stated in the above, the photosensitive materials of the present invention are suitable as photolithographic resists for the production of semiconductors utilizing ultraviolet light, deep ultraviolet light, X-ray and electron beam as light source. Because of the very high resistance to dry etching, the photosensitive materials of the present invention can be used in a form of very thin films, which provide very high level of resolution and sensitivity.

What is claimed is:

1. A photosensitive material comprising fullerene in the same layer or in contact with a photosensitive agent having at least one photosensitive group wherein the photosensitive agent is an azido compound.

2. The photosensitive material as defined in claim 1 wherein the azido compound is at least one member selected from the group consisting of 4-azidobenzalacetophenone, 4-azidobenzal- 4'-methylacetophenone, 4-azidobenzal-4'-methoxyacetophenone, 4,4'-diazidobenzalacetophenone, 4-azidobenzophenone, 2,6-di(4'-azidobenzal)cyclohexanone, 2,6-di(4'-azidobenzal)-4-methylcyclohexanone, 2,6-di(4'-azidobenzal)- 4-t-amylcyclohexanone, 4,4'-diazidodiphenylsulfone, 4,4'-diazidodiphenylether, 4,4'-diazidophenylsulfide and 4,4'-diazidodiphenylmethane.

3. The photosensitive material as defined in claim 2 wherein the azido compound is at least one member selected from the group consisting of 4,4'-diazidobenzalacetophenone, 4-azidobenzophenone, 2,6-di(4'-azidobenzal)cyclohexanone, 2,6-di(4'-azidobenzal)-4-methylcyclohexanone, 2,6-di(4'-azidobenzal)- 4-t-amylcyclohexanone, 4,4'-diazidodiphenylsulfone, 4,4'-diazidodiphenylether, 4,4'-diazidophenylsulfide and 4,4'-diazidodiphenylmethane.

4. A photosensitive material comprising fullerene which has been modified to contain at least one photosensitive group, or is in the same layer or in contact with a photosensitive agent containing at least one photosensitive group, wherein the kind of photosensitive material is a crosslinking photosensitive material (negative) or a disintegrating photosensitive material (positive).

5. The photosensitive material as defined in claim 4 wherein the kind of the photosensitive material is a crosslinking photosensitive material (negative).

6. A photosensitive material comprising fullerene which has been modified to contain at least one photosensitive group, or is in the same layer or in contact with a photosensitive agent containing at least one photosensitive group, wherein the photosensitive group is one which causes chemical reaction as a result of irradiation with ultraviolet light, deep ultraviolet light, X-ray, and electron beam.

7. The photosensitive material as defined in claim 6 wherein the photosensitive group is at least one member selected from the group consisting of an acryloyl group, a methacryloyl group, a vinyl group and an epoxy group.

8. The photosensitive material as defined in claim 7 wherein the photosensitive group is an acryloyl group and/or a methacryloyl group.

9. A photosensitive material comprising fullerene in the same layer or in contact with a photosensitive agent having at least one photosensitive group wherein the photosensitive agent having two or more photosensitive groups in the molecule thereof which causes chemical reaction as a result of irradiation with ultraviolet light, deep ultraviolet light, X-ray, or electron beam.

* * * * *